United States Patent [19]

Bishop

[11] Patent Number: 4,697,088

[45] Date of Patent: Sep. 29, 1987

[54] METHOD OF AND APPARATUS FOR DISCRIMINATING SHARP EDGE TRANSITIONS PRODUCED DURING OPTICAL SCANNING OF DIFFERENTLY REFLECTIVE REGIONS

[75] Inventor: Robert Bishop, Brookline, Mass.

[73] Assignee: Beltronics, Inc., Brookline, Mass.

[21] Appl. No.: 747,997

[22] Filed: Jun. 24, 1985

[51] Int. Cl.$^4$ ............................................. G01B 11/10
[52] U.S. Cl. ..................................... 250/561; 356/386
[58] Field of Search ............... 250/560, 561; 356/386, 356/387; 358/107; 382/8; 364/153

[56] References Cited

U.S. PATENT DOCUMENTS

| | | | |
|---|---|---|---|
| 4,269,515 | 5/1981 | Altman | 356/387 |
| 4,332,475 | 6/1982 | Demarest | 356/386 |
| 4,430,750 | 2/1984 | Koellensperger | 382/8 |

Primary Examiner—David C. Nelms
Assistant Examiner—S. Allen

Attorney, Agent, or Firm—Rines and Rines, Shapiro and Shapiro

[57] ABSTRACT

A method of and apparatus for discriminating sharp edge transitions produced during optical scanning, as by a CCD or the like, of differently reflective regions of a surface, such as copper conductors and resist background on printed circuit boards and similar applications, through delaying N successive sampling signals defining the edge transition of the desired edge transition regions slope and amplitude from unwanted reflections from other regions, subtracting each camera scan sampling signal from the previous Nth sample signal to produce a large difference signal only for the edge transitions, and adding such difference to the camera output signals to provide a distinctive boost to the edge transition signals which are then thresholded in a manner to insure rejection of signals from unwanted or spurious reflection regions into binary output signals unambiguously indentifying the edge transitions.

6 Claims, 7 Drawing Figures

ILLUMINATION

HIGH BOOST OF CAMERA OUTPUT

CAMERA OUTPUT

METHOD OF AND APPARATUS FOR DISCRIMINATING SHARP EDGE TRANSITIONS PRODUCED DURING OPTICAL SCANNING OF DIFFERENTLY REFLECTIVE REGIONS

BACKGROUND OF THE INVENTION

The present invention relates to techniques for discriminating sharp edge transitions produced during the optical scanning of differently reflective regions as, for example, in the CCD or similar camera or sensor scanning of conductors on printed circuit boards and other applications similarly involving differently reflective regions of a surface.

Considering, for illustrative purposes, the abovementioned application of CCD scanning of printed circuit boards, the scanning signal processing from the CCD must umambiguously detect the transition between, for example, copper lines and background of resist in order to enable the inspection of the integrity of the lines. Spurious reflection variations, however, as from tarnish spots or the like on the copper often provide false indications. It is to the problem of improving and, indeed, enabling the discriminating of sharp edge transitions between the differently reflective regions of the board, represented in this example by the transition between the copper and the background, with insensitivity to or irrespective of the presence of subsequent spurious reflection variations in these regions such as those caused by tarnish or the like, that the present invention is principally directed.

SUMMARY OF THE INVENTION

An object of the invention, accordingly, is to provide a new and improved method of and apparatus for discriminating such sharp edge transitions even in the presence of spurious reflection variations.

A further object is to provide a novel signal processing technique, while particularly useful for CCD and similar scanning image inspection applications, is also more generally useful in edge transition detection, as well.

Other and further objects will be explained hereinafter and are more particularly pointed out in the appended claims.

In summary, however, from one of its broader aspects, the invention provides a method of discriminating sharp edge transitions produced during the scanning of differently reflective regions on a surface with insensitivity to subsequent spurious reflection variations in said regions, that comprises, scanning the surface to produce an output having one or more spaced pairs of sharp edge transitions each defining high-amplitude impulses representing highly reflective regions spaced along the surface; converting said output into digital sampling signals; continually delaying N successive sampling signals, where N represents the number of sample signals necessary to define the edge transition region, with N being selected as the number of samples required to define discrimination between the highly reflective regions and subsequent spurious reflection variations of different slope and amplitude characteristics; subtracting each sample signal from the previous Nth sample signal whereby the edge transitions only will be indicated by a large difference signal; adding the difference and output signals such that only the edge transitions will be distinctively boosted; and comparing the added signals with high and low thresholds, selected to insure rejection of the spurious reflection signals, to generate a binary "one" for the duration of each pair of sharp edge transitions and a "zero" between each pair. A preferred embodiment and details of a best mode of carrying out the invention are herein presented.

BRIEF DESCRIPTION OF THE DRAWINGS

The invention will be described with reference to the accompanying drawings

DESCRIPTION OF THE DRAWINGS

Figure 1A:
FIG. 1A of which represents successive scanned regions of the illustrative circuit board providing transitions between copper conductors and the laminate or resist background reflections which are produced by an illumination source, FIG. 1B.
Figure 1B:
FIGS. 1C, 1D and 1E are waveform diagrams illustrating, respectively, the CCD camera output with sampling points (FIG. 1C) a high boost of the camera output (FIG. 1D), the high and low thresholding of the boosted output (FIG. 1E), and the sharply discriminating copper-laminate transition detection (FIG. 1F)

Referring to FIG. 1, an illustrative sequence is shown of conductor-resist transitions encountered in the optical reflection scanning of a printed circuit board, or, more generally, a surface having regions that provide different reflections when illuminated by a source, FIG. 1B, shown of nearly uniform slightly varying intensity. The resulting CCD camera output is shown in FIG. 1C as analog amplitude variations with time during the scan. One or more spaced pairs of sharp edge transitions each defining high-amplitude impulses I that represent the highly reflective (conductor) regions spaced along the board surface, are produced. These are converted into digital signals by the A/D converter 2 of FIG. 2. In accordance with the methodology underlying the invention, unlike standard high-boost thresholding that just finds edges, a number of samples is determined N (shown as three dots $D_1$, $D_2$, $D_3$ on the left-hand transition region of the first impulse I of FIG. 1C) necessary or adequately to define or characterize the slope of the edge transition to be detected between the background and the conductor for the desired discrimination between the scanned conductor or other material and subsequent spurious reflection variations, and vice versa. The desired edge transition region is defined in terms of both steepness of slope and sufficient amplitude to discriminate from spurious reflection signals that have both different (often lesser) slope and lesser amplitude, and that also discriminates between materials of different reflective properties. These N successive sampling signals of the order of 3 or a few (say 2–4, or so), are delayed on a continual basis in delay circuit 4 so that the output thereof is the $S_{n-N}$ sample, where $S_n$ is the originally inputed camera samples $S_n$ from the A/D converter 2.

Figure 1D:
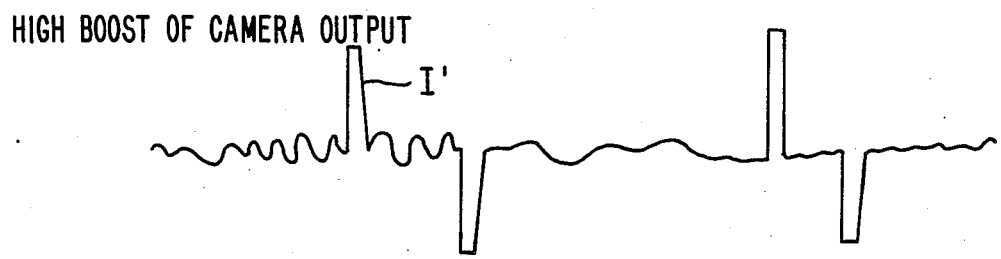
Figure 1C:
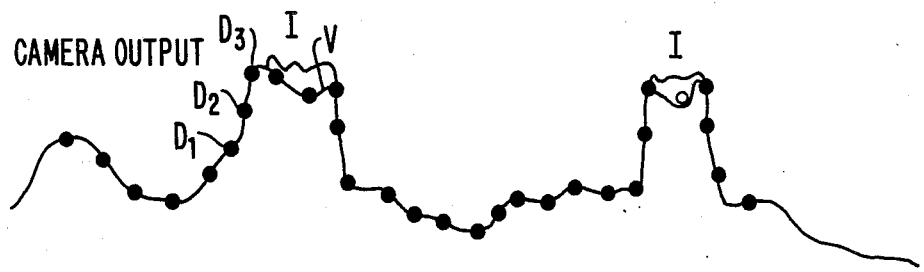
Figure 1E:
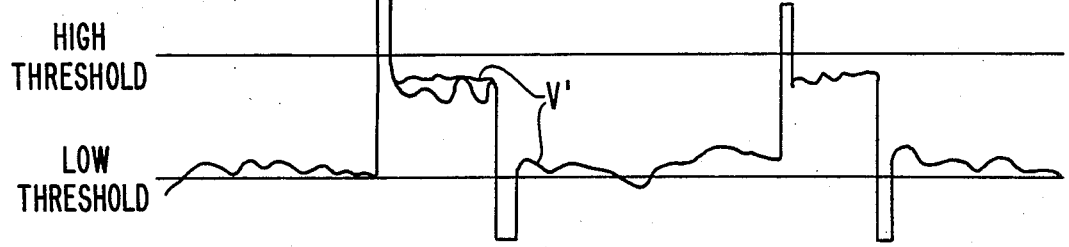
Figure 1F:
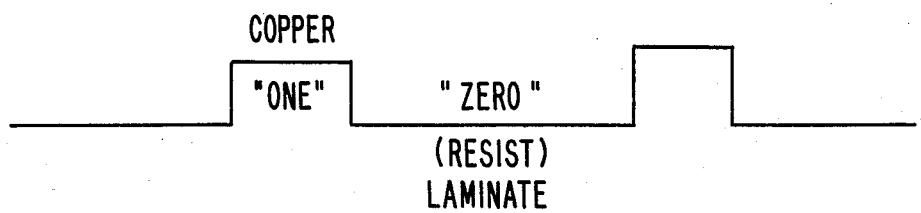
Figure 2:
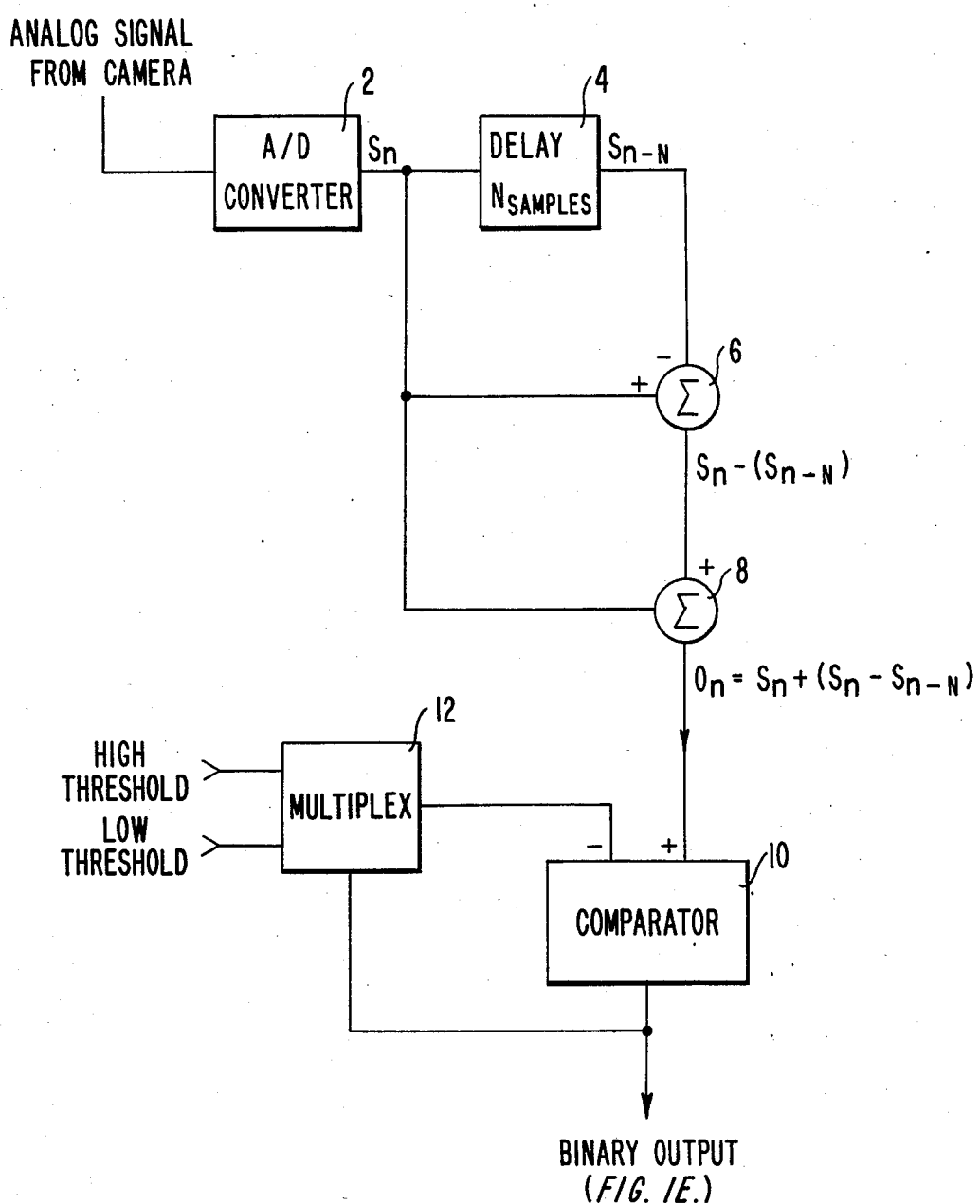
FIG. 2 is a schematic circuit and block diagram of a preferred circuit apparatus for practicing the method of the invention.

The difference between $S_n$ and $S_{n-N}$ is obtained in the subtraction circuit 6 which thus subtracts each sample signal from the previous Nth sample signal, whereby the edge transitions only will be unambiguously indicated by a large difference signal. This difference signal is then added to the camera output signal samples $S_n$ in the adder or summer 8 to produce an output $O_n = 2S_n - S_{n-N}$, so that only the edge transition regions of the desired material are distinctively boosted as shown in FIG. 1D at I'. This, moreover, is now independent or irrespective of, and insensitive to, any subsequent spurious reflection signal variations V, FIG. 1C, that may be caused by copper tarnish, specular reflection or other effects, since it is the transition edge only that receives this boost. The boosted or added output signals, FIG. 1D, are then applied to a comparator 10, FIG. 2, for comparison with hysteresis provided at 12 by multiplexed high and low threshold reference signals applied to the comparator and selected to insure rejection of the spurious reflection signals $V^1$, FIG. 1E, to generate a clean binary output wherein, preferably a binary "one" is produced for the duration of each pair of sharp edge transitions, FIG. 1F, and a "zero" between each pair.

The combination of the selection of N and the selection of the high and low threshold reference signals thus effectively acts as a spatial filter that extracts the transition signals reflected from the desired surface materials independently of perturbated or spurious or undesired reflected signals (tarnish, specular, etc).

In actual circuit implementation of this technique, high and low threshold voltages of the order of 10% and 90% of the original camera output signals were employed with booster signals in which the transitions pulse was boosted to the order of 50% of the original camera output signal at the copper scan region. Suitable components may be an A/D converter of the type AD 9000 of Analog Devices, Inc., a delay circuit comprised by a number of 74F374 (Fairchild) latches, a comparison chip of the type 74S85 (Texas Instruments) and a multiplex chip of the type 74F251 (Fairchild).

Further modifications will occur to those skilled in this art and such are considered to fall within the spirit and scope of the invention as defined in the appended claims.

What is claimed is:

1. A method of discriminating sharp edge transitions produced during the scanning of differently reflective regions on a surface with insensitivity to subsequent spurious reflection variations in said regions, that comprises, scanning the surface to produce an output having one or more spaced pairs of sharp edge transitions each defining impulses representing relatively highly reflective regions spaced along the surface; converting said output into digital sampling signals; continually delaying N successive sampling signals where N represents the number of sample signals necessary to define the edge transition region, with N being selected as the number of samples required to define the slope of the transition region for the desired discrimination between the highly reflective regions and subsequent spurious reflection variations of different slope and amplitude characteristics; subtracting each sample signal from the previous Nth sample signal to produce a substantial difference signal indicating an edge transition; adding each difference signal and a corresponding sample signal such that only the edge transitions will be emphasized; and comparing the added signals with first and second thresholds that are selected to insure rejection of spurious reflection signals, to generate a binary "one" for the duration of each pair of sharp edge transitions and a "zero" between each pair.

2. A method as claimed in claim 1 and in which the scanning is performed so as to scan a printed circuit board with copper conductors that comprise the said highly reflective regions, and so that said spurious reflection variations may be produced by copper tarnish spots, specular reflection and different materials and the like.

3. A method as claimed in claim 1 and in which N is about three.

4. Apparatus for discriminating sharp edge transitions produced during the scanning of differently reflective regions on a surface with insensitivity to subsequent unwanted reflection variations in said regions having, in combination, an optical scanning camera for scanning the surface to produce an output having one or more spaced pairs of sharp edge transitions each defining impulses representing relatively highly reflective regions spaced along the surface; analog-to-digital converter means for converting said output into digital sampling signals; delay means for continually delaying N successive sampling signals, where N represents the number of signals necessary to define the edge transition and to discriminate the slope and amplitude characteristics of the edge transition regions from those produced by unwanted reflections; means for subtracting each sample signal from the previous Nth sample signal to produce a substantial difference signal indicating an edge transition; summing means for adding each difference signal and a corresponding sample signal such that only the edge transitions will be emphasized; and comparator means for comparing the added signals with first and second thresholds to generate a binary "one" for the duration of each pair of sharp edge transitions and a "zero" between each pair, said thresholds being adjusted to insure rejection of the unwanted signals.

5. Apparatus as claimed in claim 4 and in which N is adjusted to about three.

6. A method of discriminating sharp edge transitions produced during optical scanning, as by a CCD camera, of differently reflective regions of a surface, such as copper conductors and resist background on printed circuit boards, that comprises, delaying N successive sampling signals defining the slope and amplitude of edge transisions of desired reflective transition regions from unwanted reflections from other regions; subtracting each camera scan sampling signal from the previous Nth sample signal to produce a large difference signal only for the edge transitions; adding each difference to a corresponding camera output signal to emphasize to the edge transition signals; and then thresholding the same in a manner to insure rejection of signals from unwanted or spurious reflection regions to generate binary output signals unambiguously indentifying the edge transitions.

* * * * *